US005484399A

United States Patent [19]

DiResta et al.

[11] Patent Number: 5,484,399
[45] Date of Patent: Jan. 16, 1996

[54] PROCESS AND DEVICE TO REDUCE INTERSTITIAL FLUID PRESSURE IN TISSUE

[75] Inventors: Gene R. DiResta, Yonkers; Jongbin Lee, Astoria, both of N.Y.; Ehud Arbit, Englewood, N.J.

[73] Assignee: Sloan-Kettering Institute for Cancer Research, New York, N.Y.

[21] Appl. No.: 181,356

[22] Filed: Jan. 13, 1994

Related U.S. Application Data

[63] Continuation of Ser. No. 842,267, Feb. 27, 1992, abandoned.
[51] Int. Cl.⁶ ............................................. A61N 1/30
[52] U.S. Cl. ............................... 604/21; 604/173; 128/748
[58] Field of Search .................................. 604/19, 21, 49, 604/173, 902; 128/748

[56] References Cited

U.S. PATENT DOCUMENTS

| | | | |
|---|---|---|---|
| 3,191,600 | 6/1965 | Everett | 604/902 |
| 3,430,628 | 3/1969 | Wiggins | 604/173 |
| 4,192,319 | 3/1980 | Hargens | 128/748 |
| 4,423,740 | 1/1984 | Castle et al. | 128/748 |
| 4,692,153 | 9/1987 | Berlin et al. | 604/21 |
| 4,739,769 | 4/1988 | Matthews et al. | 128/748 |
| 4,792,328 | 12/1988 | Beck et al. | 604/49 |
| 4,878,900 | 11/1989 | Sundt | 604/902 |
| 4,913,698 | 4/1990 | Ito et al. | 604/22 |

FOREIGN PATENT DOCUMENTS

| | | | |
|---|---|---|---|
| 2309242 | 5/1975 | France | 604/173 |

OTHER PUBLICATIONS

Algire, G. H., Legallais, F. Y., *Journal of the National Cancer Institute*, (1951), vol. 12, No. 1, pp. 399–421, (Exhibit 2).
Aukland K., et al., *Circulation Research*, (1964), vol. 14, pp. 164–187, (Exhibit 3).
Baxter, L. T., Jain, R. K., *Microvascular Research*, (1989), vol. 37, pp. 77–104, (Exhibit 4).
Butler, T. P., et al., *Cancer Research*, (1975), vol. 35, pp. 512–516, (Exhibit 5).
Cheung, N. K. V., et al., *Cancer Research*, (1985), vol. 45, pp. 2642–2649, (Exhibit 6).
Cliff, W. J., *Quarterly Journal of Experimental Physiology And Cognate Medical Sciences*, (1965), vol. 50, pp. 79–89, (Exhibit 7).
DiResta, G. R., et al., *American Journal of Physiology*, (1987), vol. 16, No. 4, pp. G573–G581, (Exhibit 8).
Eddy, H. A., Casarett, G. W., *Microvascular Research*, (1973), vol. 6, No. 1, pp. 63–82, (Exhibit 9).
Gerlowski, L. E., Jain, R. K., *Microvascular Research*, (1986), vol. 31, No. 3, pp. 288–305, (Exhibit 10).
Hammersen, F., in: *Capillary Permeability*, Crone, C., Lassen, N. A., editors, Academic Press, New York, (1970), pp. 351–365, (Exhibit 11).
Hauck, G., *Angiologica*, (1971), vol. 8, pp. 236–260, (Exhibit 12).
Hori, K., et al., *Japanese Journal Center Research (Gann)*, (1986), vol. 77, No. 1, pp. 65–73, (Exhibit 13).

(List continued on next page.)

*Primary Examiner*—Corrine M. Maglione
*Attorney, Agent, or Firm*—John P. White

[57] ABSTRACT

A method and apparatus are provided for reducing interstitial fluid pressure in tissues, particularly in tumors, by applying suction to the interior of the tissue. The method comprises inserting into the tissue one or more needle-like, elongated tubes, each having at least one hole at or near the end that is inserted into the tissue and each having means to apply suction to the protruding end. The reduced pressure produced inside the tissue by this method is useful to: facilitate penetration by drugs and therapeutic macromolecules into the tissue; enhance radiation treatment of tumors by increasing the oxygen supply in the tumor; and remove fluid to reduce edema in tissues, e.g. brain edema. Means may be provided to measure the pressure within the tissue and to use this measurement to control the suction applied to the tissue through the tubes.

9 Claims, 7 Drawing Sheets

OTHER PUBLICATIONS

Ide, A. G., et al., *The American Journal of Roentgenology and Radium Therapy*, (1939), vol. 42, No. 6, pp. 891–899, (Exhibit 14).

Intaglietta, M., et al., *American Journal of Physiology*, (1971), vol. 221, No. 3, pp. 922–928, (Exhibit 15).

Jain, R. K., *Cancer Research*, (1987), vol. 47, No. 12, pp. 3039–3051, (Exhibit 16).

Jain, R. K., *Journal of the National Cancer Institute*, (1989), vol. 81, No. 8, pp. 570–576, (Exhibit 17).

Jain, R. K., *Cancer Research*, (1988), vol. 48, pp. 2641–2658, (Exhibit 18).

Jain, R. K., *Cancer Research*, (Supplement), (1990), vol. 50, No. 3, pp. 814s–819s, (Exhibit 19).

Jain, R. K., *Biotechnology Progress*, (1985), vol. 1, No. 2, pp. 81–94, (Exhibit 20).

Jain, R. K., *Cancer and Metastasis Reviews*, (1990), vol. 9, pp. 253–266, (Exhibit 21).

Jain, R. K. Baxter, L. T., *Cancer Research*, (1988), vol. 48, pp. 7022–7032, (Exhibit 22).

Köhler, G., and Milstein, C., *Nature*, (1975), vol. 256, No. 5517, pp. 495–497, (Exhibit 23).

Koshu, K., et al., *Stroke*, (1982), vol. 13, No. 4, pp. 483–487, (Exhibit 24).

Lockwood, A. H., Kemp, P. J., *Stroke*, (1981), vol. 12, No. 2, pp. 173–176, (Exhibit 25).

Neuwelt, E. A, et al., *Neurosurgery*, (1987), vol. 20, No. 6, pp. 885–895, (Exhibit 26).

Ogston, A. G., Michel, C. C., in *Progress In Biophysics And Molecular Biology*, Noble, D., editor, (1978), vol. 34, pp. 197–217, (Exhibit 27).

Paskins–Hurlburt, A. J., et al., *Microvascular Research*, (1982), vol. 24, pp. 15–24, (Exhibit 28).

Peters, W., et al., *Journal of the National Cancer Institute*, (1980), vol. 65, No. 3, pp. 631–642, (Exhibit 29).

Phelps, M. E., et al., *Journal of Nuclear Medicine*, (1978), vol. 19, No. 12, pp. 1311–1319, (Exhibit 30).

Roberts, P. A., et al., *Journal of Neurosurgery*, (1987), vol. 66, pp. 440–446, (Exhibit 31).

Shenkin, H. A., et al., *Journal of Neurosurgery*, (1962), vol. 19, No. 10, pp. 897–901, (Exhibit 32).

Stosseck, K., Lübbers D. W., Cottin, N., *Pflügers Archiv—European Journal of Physiology*, (1974), vol. 348, pp. 225–238, (Exhibit 33).

Warren, B. A., *Microvascular Research*, (1970), vol. 2, pp. 443–453, (Exhibit 34).

Wiig, H., et al., *Scandinavian Journal of Clinical & Laboratory Investigation*, (1982), vol. 42, No. 2, pp. 159–164, (Exhibit 35).

Wikstrand, C. J., and Bigner, D. D., *Cancer Research*, (1982), vol. 42, No. 1, pp. 267–275, (Exhibit 36).

Wilkinson, G. R., Shand, D. G., *Clinical Pharmacology and Therapeutics*, (1975), vol. 18, No. 4, pp. 377–390, (Exhibit 37).

Yamaura, H., Sato, H., *Journal of the National Cancer Institute*, (1974), vol. 53, No. 5, pp. 1229–1240, (Exhibit 38).

Young, J. S., Griffith, H. D., *Journal of Pathology and Bacteriology*, (1950), vol. 62, No. 3, pp. 293–311, (Exhibit 39).

Baxter, L. T., and Jain, R. K., *Microvascular Research*, (1990), vol. 40, pp. 246–263, (Exhibit 40).

Baxter, L. T., and Jain, R. K., *Microvascular Research*, (1991), vol. 41, pp. 5–23, (Exhibit 41).

Baxter, L. T., and Jain, R. K., *Microvascular Research*, (1991), vol. 41, pp. 252–272, (Exhibit 42).

Boucher, Y., Baxter, L. T., Jain, R. K., *Cancer Research*, (1990), vol. 50, pp. 4478–4484, (Exhibit 43).

Boucher, Y., et al., *Cancer Research*, (1991), vol. 51, No. 24, pp. 6691–6694, (Exhibit 44).

Roh, H. D., et al., *Cancer Research*, (1991), vol. 51, No. 24, pp. 6695–6698, (Exhibit 45).

Leunig, M., et al., *Cancer Research*, (1992), vol. 52, pp. 487–490, (Exhibit 46).

PROCESS AND DEVICE TO REDUCE INTERSTITIAL FLUID PRESSURE IN TISSUE

This is a continuation of application Ser. No. 07/842,267, filed Feb. 27, 1992 now abandoned.

BACKGROUND OF THE INVENTION

The present invention relates to a method and apparatus for reducing interstitial fluid pressure in tissue, particularly in tumors, and for removing interstitial fluid from confined spaces where drainage of such fluids is impaired, such as to reduce edema accumulation.

Throughout this application various publications are referenced and citations are provided in parentheses. The disclosure of these publications in their entireties are hereby incorporated by reference into this application in order to more fully describe the state of the art to which this invention pertains.

Cancer is the second leading cause of death in this country and still continues to be a public health problem of increasing significance (28). Cancer therapy may be categorized into three major approaches, surgical excision, radiotherapy and chemotherapy. Chemotherapy is defined as the treatment of cancer by a systemic administration of drugs.

Unfortunately, most drugs that showed promising effects in vitro have failed to be as effective in vivo, particularly in solid tumors. It has recently been proposed that one of the major reasons for this failure is the impediment of drug transport into tumors. In particular, a physiological barrier created by raised interstitial fluid pressure appears to be responsible. The interstitial fluid pressure is raised in tumors primarily because of the lack of lymphatics in tumors and the growth in confined spaces. The raised interstitial fluid pressure in tumors is a principal transport-retarding factor for the delivery of drugs such as macromolecules, i.e. large molecular weight molecules such as monoclonal antibodies (MoAb), tumor nucrosis factor and other chemotherapeutic agents.

Interstitial fluid accumulation is a known phenomenon in peritumoral areas in the brain and other organs, and where an adequate drainage system such as a lymphatic system is absent. This invention is aimed to facilitate clearance of interstitial fluid in circumstances such as brain edema from a variety of causes or lymphedema in the limbs after procedures such as mastectomy or lymphadenectomy.

Toxicity to normal tissues limits both the dose and frequency of drug administration. Antibody targeting specific tumor-associated antigens reduced some of the side effects of chemotherapy. Since the discovery of hybridoma technology by Kohler, G. and Milstein, C. (24), the application of MoAbs has rejuvenated efforts with chemotherapeutic treatment of tumors inaccessible as well as inoperable by moderate techniques. The monomer forms of basic immunoglobulin molecules range from 150 to 180 kd (4).

Use of MoAbs in the treatment of cancer is potentially very attractive. MoAbs bind very specifically to antigens. In cancer treatment, the theory is to use MoAbs that are specific to tumor-associated antigens. In attempts to enhance or extend therapeutic and diagnostic applications of MoAbs, MoAbs have been conjugated with radionuclides, toxins, drugs, cytokines, enzymes, effector antibodies, growth factors, biological response modifiers, extracellular matrix peptide products, immunotoxins, lymphokine activated killer cells, and tumor-infiltrating lymphocytes. (19).

MoAb therapy using conjugated pharmaceuticals, however, has not lived up to early expectations due to problems of hindered transport or delivery of MoAbs to tumors (See, e.g., 19, 21). Numerous factors can affect MoAb delivery. Jain et al. (16, 17, 18, 21) have emphasized the importance of an Interstitial Fluid Pressure (IFP) barrier against the effective transport of macromolecules such as MoAbs.

The large permeability resulting from the number of fenestrated capillaries and low hyaluronic acid content in the tumor interstitial fluid should, in principle, improve the transport of therapeutic drugs. In reality, however, the delivered fraction of infused dosage has not been up to the expected level. Heterogeneous blood flow, binding hindrance at the cell surface and heterogeneous antigen distribution, particularly in MoAb delivery, are not reasons enough to explain retarded transport in tumor tissue (22).

Jain et al. (19, 21) suspected that elevated Interstitial Fluid Pressure (IFP) is a principal transport retarding factor in MoAb delivery because of the lack of lymphatics in the tumor. In normal tissue, maintenance of the fluid balance within the tissue spaces is dependent upon the interplay of hydrostatic and colloid osmotic pressures operating on a vascular network with uneven permeability and with dissimilar exchange area with the aid of the lymphatic system. The lymphatics are responsible for macromolecular circulation throughout the body. Most macromolecules including proteins cannot return to the circulation without the lymphatic system after they percolate through the endothelial wall (11). Accordingly, lymphatic drainage is a factor of primary importance in maintaining fluid balance (12). Once the equilibrium is disrupted, dehydration or edema in the tissue would result from the imbalanced colloid osmotic and hydrostatic vascular pressure. These relations are well described by Starling's hypothesis (29).

A functioning lymphatic system as an anatomical entity has not been demonstrated in the tumor. The absence of lymphatics affords no alternative way circulating macromolecules can re-enter the circulation after their extravasation through capillary. The potential of fluid flow into the tumor is hindered by the opposing force with equivalent magnitude from IFP. This opposite force increases the IFP until all the forces in Starling's Law are balanced. Consequently, the interstitial fluid within the tumor becomes trapped. The fluid with MoAb therapeutic agents has insufficient force to flow into the tumor except for the slow advance by molecular diffusion because of a concentration gradient. Instead, it oozes out toward the tumor surface by the effective convection, diffusion and draining advantage by lymphatics at the tumor periphery. This outward fluid velocity at the tumor periphery additionally hinders the diffusional movement of molecules into the tumor center (19). Decreased intravascular pressure and/or increased interstitial pressure in tumors has been demonstrated by several investigators (1, 9, 14, 31, 37, 41).

Findings to date indicate that elevated IFP has been attributed to the absence of a well-defined lymphatic system in the tumor (5, 21), and to increased permeability of tumor vessels (16, 20). Researchers reported that IFP increases with tumor size (13, 30, 38, 42). The increase in IFP has also been shown to correlate with reduction in tumor blood flow (lower blood perfusion rate) and the development of necrosis in a growing tumor (13, 15, 30, 38).

Jain et al. (22) presented a mathematical model describing the possible relationship between the distribution of monoclonal antibody and elevated interstitial pressure. They proposed that enhanced IFP might be responsible for the poor penetration of MoAbs into tumors including the heterogeneous blood perfusion, hindered diffusion in the interstitium, and extravascular binding of MoAbs. Furthermore, they stated that the elevated interstitial pressure principally reduces the driving force for extravasation of fluid and macromolecules in tumors, and leads to an experimentally verifiable, radially outward convection which opposed the inward diffusion. They have presented results from several mathematical models and the models' implications (3, 17, 19, 21) to support their hypothesis.

Several investigators (10, 23, 32, 34) have attempted to increase Blood Perfusion Rate (BPR) via administration of vasoactive agents such as angiotensin and interleukin. In addition, radiation and heat treatment has been shown to increase the tumor blood flow. A key problem with these approaches is that the increase in blood flow is short-lived and usually confined to well vascularized regions (17, 19, 21). Osmotic agents as mannitol have also been used to reduce IFP by exerting higher vascular osmotic pressure (17, 19, 21, 33).

SUMMARY OF THE INVENTION

An object of the present invention is to provide a new mechanical approach to decrease IFP, and/or facilitate clearing of interstitial fluid when such clearing is impaired (e.g., brain edema, lymph edema). According to the present invention, an artificial lymphatic system (ALS) is employed to reduce IFP within tissue, particularly tumors. The object is to enhance convection through the tumor by creating a new pressure gradient within the tumor. For reducing IFP in tumors, a suction force is used to create a negative pressure (less than the IFP) inside the tumor.

The method and apparatus of this invention will be suitable for reducing IFP for inoperable tumors (including brain and liver tumors) as well as operable tumors, and thereby enhance penetration of drugs, in particular macromolecules (e.g. MoAbs), into tumors.

It is another object of the present invention to reduce interstitial fluid pressure in tumors, to thereby enable blood to be drawn into the tumor, which blood will transport oxygen into the tumor and enhance radiation treatment of the tumor.

It is another object of the present invention to provide an adjunct treatment to chemotherapy involving large macromolecules.

According to one aspect of the present invention, a process for reducing interstitial fluid pressure in tissue is provided, comprising placing an aspiration device within tissue, and applying, to the aspiration device, suction having a pressure value less than the interstitial fluid pressure, to thereby reduce the interstitial fluid pressure within the tissue.

According to another aspect of the present invention, an apparatus for reducing interstitial fluid pressure in tissue is provided, comprising an aspiration device having a plurality of aspiration tubes connected to a manifold means, each of said tubes having a plurality of aspiration holes, and means for connecting the manifold means to a suction source for creating suction inside the aspiration tubes, having a pressure value less than the interstitial fluid pressure to thereby reduce the fluid pressure inside the tissue when the tubes are located in the tissue.

According to another aspect of the invention, a process for reducing interstitial pressure in and withdrawing fluid from tissue is provided, comprising placing an aspiration device within tissue having excess fluid accumulation, and applying, to the aspiration device, suction having a pressure value less than the interstitial pressure, to thereby reduce interstitial pressure and withdraw fluid from the tissue.

Other objects and advantages will become apparent from the detailed description, claims and accompanying drawing.

DETAILED DESCRIPTION OF THE INVENTION

According to one aspect of the present invention, a process for reducing interstitial fluid pressure in tissue is provided, comprising placing an aspiration device within tissue, and applying, to the aspiration device, suction having a pressure value less than the interstial fluid pressure, to thereby reduce interstitial fluid pressure within the tissue.

The tissue may be a tumor. The step of placing an aspiration device preferably comprises placing an aspiration device having a plurality of aspiration holes. The step of placing an aspiration device preferably comprises placing an aspiration device having a plurality of aspiration tubes, each tube having at least one aspiration hole. The number of aspiration tubes and distance therebetween is preferably dependent on the size of the tumor. Each tube preferably has a plurality of aspiration holes. The step of applying suction may comprise applying suction having a substantially constant value. The process may include measuring the interstitial fluid pressure inside the tissue and regulating the suction applied to the aspiration device in dependence on the measured interstitial fluid pressure. The suction applied may decrease in value over time, i.e. be time varying. The aspiration device may have means for measuring the interstitial fluid pressure.

According to another aspect of the present invention, an apparatus for reducing interstitial fluid pressure in tissue is provided, comprising an aspiration device having a plurality of aspiration tubes connected to a manifold means, each of said aspiration tubes having a plurality of aspiration holes, and means for connecting the manifold means to a suction source for creating suction, inside the aspiration tubes, having a pressure value less than the interstitial fluid pressure, to thereby reduce the interstitial fluid pressure inside the tissue when the tubes are located in the tissue.

The aspiration device preferably comprises a plurality of elongated tubes each having a distal end for insertion into a tumor, the elongated tubes being arranged in parallel and being connected at their near ends to a central manifold. There may be five elongated tubes arranged with one central tube and four equally spaced peripheral tubes. The aspiration holes are formed along at least part of the length of the aspiration tubes. Preferably, suction pump means are provided, connected to the manifold means, for creating a suction. The suction pump means may be implantable. The apparatus may include means for measuring the interstitial fluid pressure inside the tissue. Control means may be provided, connected to the measurement probe and suction source, for regulating the suction created in dependence on the suction measured. The suction source may have a pressure value which is substantially constant or time-varying. The number of aspiration tubes and distance therebetween may be dependent on the size of the tumor. One of the tubes may include means for anchoring the tube inside the tissue, such as by way of having a spiral or corkscrew shape.

According to another aspect of the invention, a process for reducing interstitial fluid pressure in and withdrawing fluid from tissue is provided, comprising placing an aspiration device within tissue having excess fluid accumulation, and applying, to the aspiration device, suction having a pressure value less than the interstitial fluid pressure, to thereby reduce interstitial fluid pressure and withdraw fluid from the tissue.

Figure 1A:
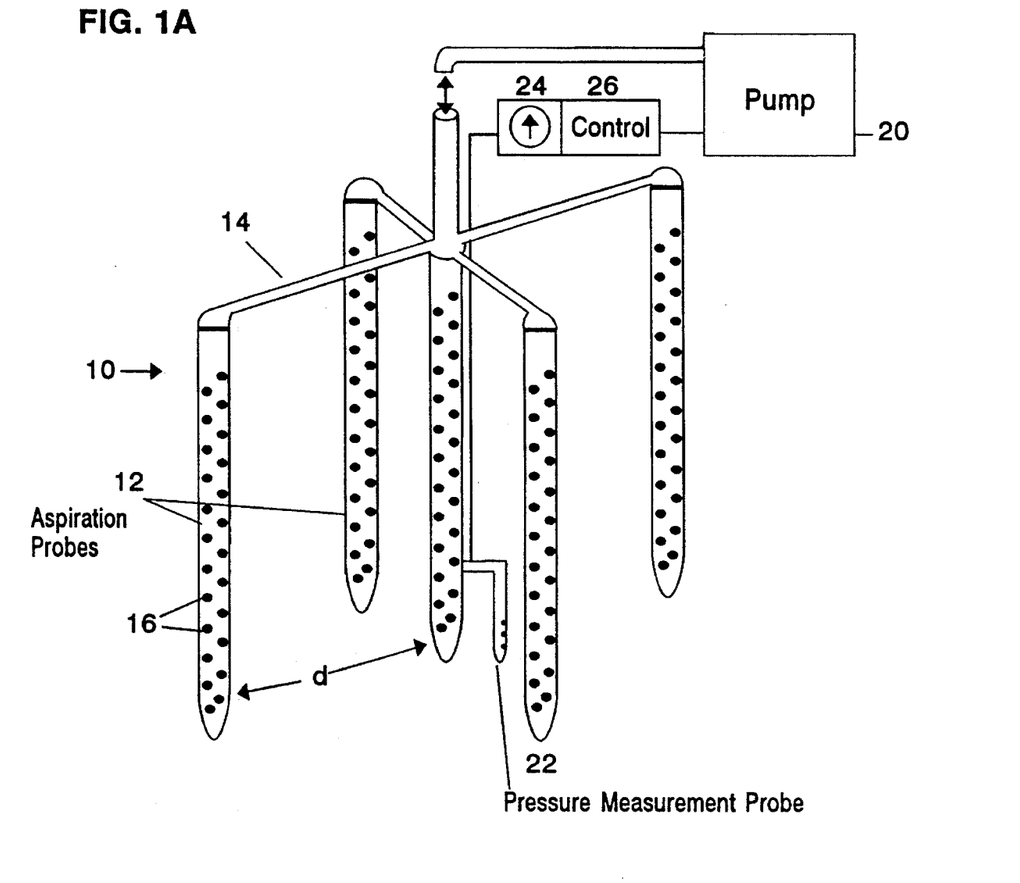
FIG. 1A is a perspective view of an aspiration device according to the invention for reducing interstitial fluid pressure.

With reference to FIG. 1A, an apparatus for reducing interstitial fluid pressure is provided, comprising an aspiration device 10 comprising a plurality of aspiration tubes 12 which terminate in a rounded cone (at the bottom of FIG. 1A). The near ends are connected to the manifold 14, which in turn is connected to a suction pump 20. The suction pump preferably generates a negative pressure selectively adjustable in the −50 to −100 mmHg range. A number of different pumps or pump systems may be used. One is the house vacuum in a hospital or the like, the suction for which can be adjustable at the patient area. Another pump arrangement is a portable suction pump, which may be the suction side of a suction/delivery pump. Yet another is an implantable pump, which can be an osmotic passive pump, or an electronic pump. Other pump arrangements will readily occur to those skilled in the art.

The aspiration device may also comprise a plurality of tubes or needles each being selectively and individually positionable inside the tissue or tumor. The tubes would be connected to a manifold or suction source using flexible conduits. Such an arrangement would enable the tubes to be placed at strategic locations inside the tumor or tissue for the best effects given the particular fluid pressure conditions and tumor/tissue conditions.

As discussed below, the IFP in a 3 cm diameter tumor has been observed to be 12.3±0.26 mm Hg at its center. As used herein, the term "suction" is intended to mean suction pressure value less than the IFP. For tumor having an IFP of 12 mm Hg at its center, "suction" would then mean a pressure of <12 mm Hg, although a sub atmospheric pressure value of e.g. −50 mm Hg would preferably be used.

The aspiration device may include a measurement probe 22 for measuring the interstitial fluid pressure. This measurement probe 22 could be attached to an aspiration tube 12, such as the central aspiration probe shown, or could replace any one of the aspiration tubes. The measurement probe could have holes only at or near the tip, and would be filled with a porous material, such as a sponge, to prevent tissue aspiration. The measurement probe 22 could be connected to a gauge 24 indicating the measured pressure, and can be connected to a feedback control means 26, which could control the applied suction of the pump in dependence on the measured pressure.

The control means would be useful not only in keeping the applied suction in a certain range, but could also conserve power, which is especially beneficial if the pump were osmotic. The pump could be turned on only when the measured suction pressure fell outside one boundary of the range and turned off when the measured suction pressure fell outside the other boundary of the range.

The target suction pressure could be substantially constant, or could be time-varying, tapering from on initial value of say −80 mm Hg toward a zero value, the trend being for example linear, exponential or step wise, and could terminate before the zero value is reached. The time-varying negative pressure control could be used if the pump were osmotic.

The aspiration device, including tubes, may be made of biocompatible material, such as rigid plastic (e.g. polyurethane or polyethylene) which is typically disposable after use, or metal, such as 316 stainless steel which can be reused. Other material may be used as will occur to those skilled in the art.

Figure 1B:
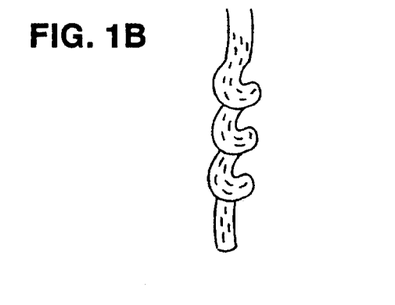
FIG. 1B shows a probe having a spiral or corkscrew shape.

The length of each tube may be on the order of 2 to 8 cm, and a set could be made available with lengths varying every 0.5 cm, from 2 to 8 cm, for example, for different size tumors. Further, the holes may be only along the end of the tube, for example along the 2 cm end of an 8 cm tube, where the tumor has a size of about 2 cm and is 6 cm or more below the entry point of the body. The diameter of the tube can be on the order of a 18 or 20 gauge needle. A factor in selecting the diameter is the bloodiness of the tumor. For relatively bloody tumors, an 18 gauge size needle or tube could be used. The tubes may be straight, but one or more can also have other shapes, such as a spiral or corkscrew shape as shown in FIG. 1B, which would aid in anchoring the probe. The hole size would be dependent on the size or length of the tubing, and would typically range from 0.1 mm to 0.5 mm. The hole size should be selected to minimize or avoid clogging. Of course, these values are exemplary and other values may be employed. The tubes may contain porous packing material to prevent tissue removal. Such a tube would be chosen for necrotic or soft tissue. The intention would be to provide a route for fluid removal or pressure relief. Tissue suction would be potentially dangerous and counter productive, i.e. bleeding, followed by clotting around or within a tube.

The efficacy of the present invention was demonstrated by the following experimental model.

EXPERIMENTAL DETAILS

I Experimental Methods

I.1 Measurement of Interstitial Fluid Pressure:

Interstitial Fluid Pressure (IFP) was measured by the Wick-In-Needle (WIN) technique (38, 39, 40), which is described more fully below.

I.2 Measurement of Blood Perfusion Rate:

The Blood Perfusion Rate (BPR) was measured using the clearance of locally generated hydrogen (CLGH) technique (2, 21, 25, 36). Stosseck et al. (36) devised a method for the measurement of cerebral blood flow using electrochemically generated hydrogen.

Temporal changes of BPR were made with the Laser Doppler Flowmetry (LDF) technique. Laser Doppler Flowmetry noninvasively measures capillary blood perfusion parameters (blood flow, volume, and velocity) in real time (8, 26, 35).

I.3 Tumor Selection:

The neuroblastoma was selected as our experimental model because it is a stabilized animal model and has a well-established monoclonal antibody. MoAb 3F8 is a murine $IgG_3$ antibody specific for the disaloganglioside $G_{D2}$, an antigen expressed on the surface of a wide spectrum of human tumors including neuroblastoma and melanoma cells (7). The MoAb was developed using human cell hybridoma technology by Cheung (6).

MoAb 3F8 are not rapidly modulated after binding with antigen. Antigenic modulation has been a major obstacle in tumor immunotherapy, especially leukemia, but despite prolonged incubation with 3F8 in vitro, the target antigen GD2 does not undergo modulation (6). These properties provide distinct advantages to MoAb 3F8 for targeting selectively to neuroblastomas in vivo.

I.4 Tumor Implantation:

Athymic nude rats ranging from about 250 to about 300 grams body weight were purchased from National Cancer Institute, fed with autoclaved rat diet, and kept under pathogen-free conditions. Suppression of the immune response against the immunologic xenograft was performed using 1.2 ml cyclophosphamide/kg body weight injected i.p. before the day of implantation. Neuroblastoma tissue were harvested from a tumor-bearing rat and chopped into cubes with the volume of 5–10 $mm^3$. These tumor tissues were stored in MEM cell culture medium until used. All the surgical instruments were sterilized by steam autoclaving.

Each animal was anesthetized by i.m. injection of a mixture of xylazine (Mobay Corp., Kansas), 80 mg/kg and ketamine (Parke-Davis, New Jersey), 5 mg/kg body weight. A pouch was created under the skin on the caudal muscles of the lower back using surgical scissors. The prepared tumor tissue was then inserted into this pouch using forceps. A surgical stapler was employed to close the opening. The rat was returned to its cage after the application of betadine preps over the surface of tumor for sterilization.

I.5 Histological Observation:

Tumors were quickly excised and frozen in Freon (La Roche Chemicals, LA) contained in a dry ice bucket. The tumor was sliced into 20 µm thick sections using a cryotome (Bright Inc., New Jersey). The sections were stained with hematoxylin and eosin (H and E), in which nuclear structures are stained dark purple or blue and practically all cytoplasmic structures and intercellular substances are stained pink (27).

Figure 2:
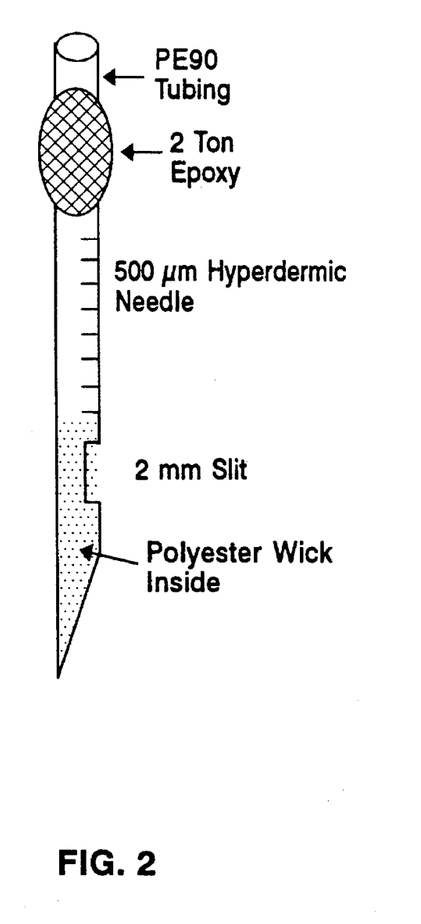
FIG. 2 is a pictorial illustration of a wick-in-needle (WIN) probe.

I.5 Interstitial Fluid Pressure:

The WIN technique for measuring IFP comprised a thin hypodermic needle (outside diameter 500 µm) with a 1–2 mm long sidehole was filled with multifilamentous polyester thread (FIG. 2). The wick material was packed to ensure a response time of two minutes or less. A polyethylene catheter, PE90, was attached to the opposite end of the WIN probe and connected to the Camino pressure transducer. WIN probes were tested using a water-head pressure regulator and subsequently treated with gas sterilization. Preconditioning was performed by filling the WIN probe with distilled water using a syringe and immersing into a chamber with distilled water a day before use. The probe was calibrated, then positioned by the guiding assembly of a Kopf stereotactic positioner. The WIN probes were advanced slowly downward toward the tumor center. At each 2 mm depth, the pressure was recorded continuously for ten minutes to ensure equilibrium with surrounding pressure.

I.6 Blood Perfusion Rate:

Tumor blood flow was measured using a clearance of locally generated hydrogen (CLGH) and Laser Doppler Flowmetry (LDF) methods. CLGH was employed to measure radial distribution of Blood Perfusion Rate (BPR). LDF was used to evaluate BPR at the surface of tumor with time while manipulating IFP or BPR.

Figure 3:
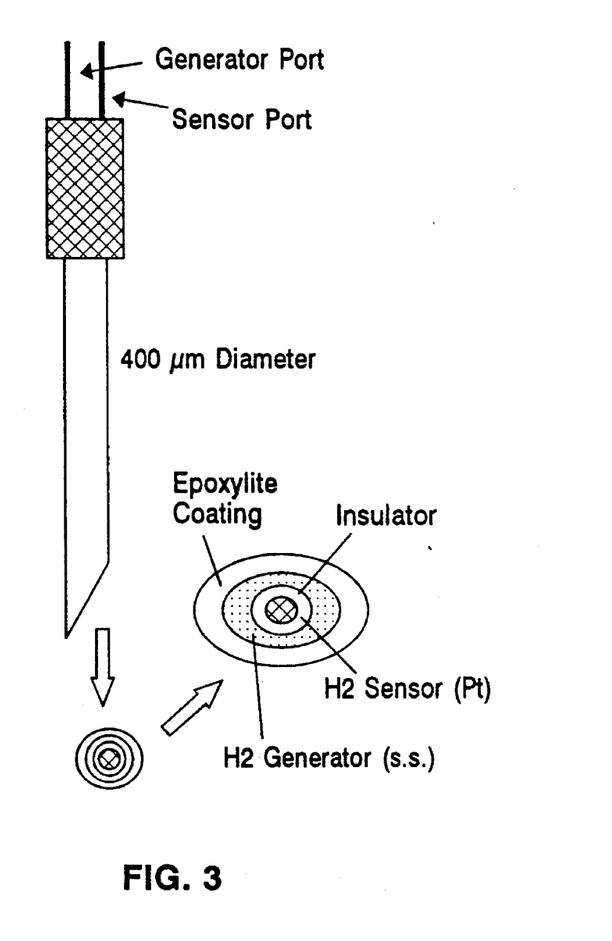
FIG. 3 is a pictorial illustration of an electrode for clearance of locally generated hydrogen (CLGH)

The CLGH method was implemented as follows: A miniaturized electrode was developed as shown FIG. 3 which could be placed in the tissue at the region of interest. As a sensor for cleared hydrogen, a Teflon coated 50 µm platinum wire was inserted through the center of 500 µm outside diameter (o.d.) stainless steel hypodermic needle and secured within the needle with "2 Ton" Epoxy (Devcon Inc., Massachusetts). The barrel of the needle was coated with Epoxylite (Epoxylite Ltd., California) for electrical insulation. The coating was removed from the tip and the assembly was polished. The barrel served as our hydrogen generator. The cylindrical geometry of generator was a unique fabrication for our experiments. It eliminated the dependence of the mean flow vector to the generator and sensor electrode orientation.

The concentration measured by the sensor reflects the diffusive-convective transport processes present in the tissue and responsible for carrying the $H_2$ away from the generator. Several minutes after the generator is turned on, the local tissue becomes saturated, that is, the sensor's response plateaus. At this point, the generator is turned off and the $H_2$ concentration declines by the local transport phenomena. The time constant reflecting the decline is directly related to an "effective" diffusion coefficient. This coefficient is in turn directly related to the capillary blood flow in the region. Quantitative flow measurement requires that the zero-flow diffusion coefficient be measured and then subtracted from the previous measurements. This value is a function of the tissue structure and temperature and was determined for each animal when it was sacrificed.

The Laser Doppler Flowmeter used in our studies was the BPM403 (Vasamedics, Inc., Minnesota) with needle and combination LDF-CLGH probes. With the combination probes, the correlation of CLGH and LDF could be evaluated. After careful removal of skin over the tumor, the LDF probe was placed using a flexible probe guider. The probe guide had a spiral wire so that it could absorb the respiratory movement artifacts.

II Experiment One

Interstitial Fluid Pressure and Blood Perfusion Rate Manipulation:

II.1 Purpose:

In our study, chemical methods using angiotensin II and mannitol were tested to examine the possibility of manipulating Interstitial Fluid Pressure (IFP) and Blood Perfusion Rate (BPR) in our tumor model. We also investigated the possibility of IFP reduction using an aspiration system to create an artificial lymphatic system (ALS).

To decrease IFP, an artificial lymphatic system (ALS) was employed to remove fluid from tumor's core by imposing suction to the center of the tumor. The object is to enhance convection through the tumor by creating a new pressure gradient within the tumor. A portable reverse water-head regulator provided a stable and continuous vacuum pressure ranging from about (−50) mmHg to about (−100) mmHg. The vacuum pressure was delivered to the center of the tumor by a 20 gauge needle through a rigid tubing system.

II.2 Experimental Procedures:

In order to examine the impacts of pharmaceutical and mechanical manipulations, IFP and BPR were measured simultaneously by WIN and LDF methods respectively. In evaluating drug effects, IFP was measured at the center of the tumor. However, when aspiration was exerted at the tumor's center, IFP was evaluated at the peripheral. BPR was measured at the surface of the tumor. After a tumor-bearing rat was anesthetized, femoral artery and vein cannulation were performed to measure blood pressure and for drug infusion respectively. Either angiotensin II, 0.5 µg/kg or mixture of the angiotensin with mannitol, 1000 mg/kg was infused with a micro-infusion pump for five minutes. In the case of aspiration manipulation, the rat was subject to aspiration after an hour of anesthesia to ensure similar physiological condition with drug groups. The vacuum pressure was continuously observed using a Camino pressure monitor.

Figure 4:
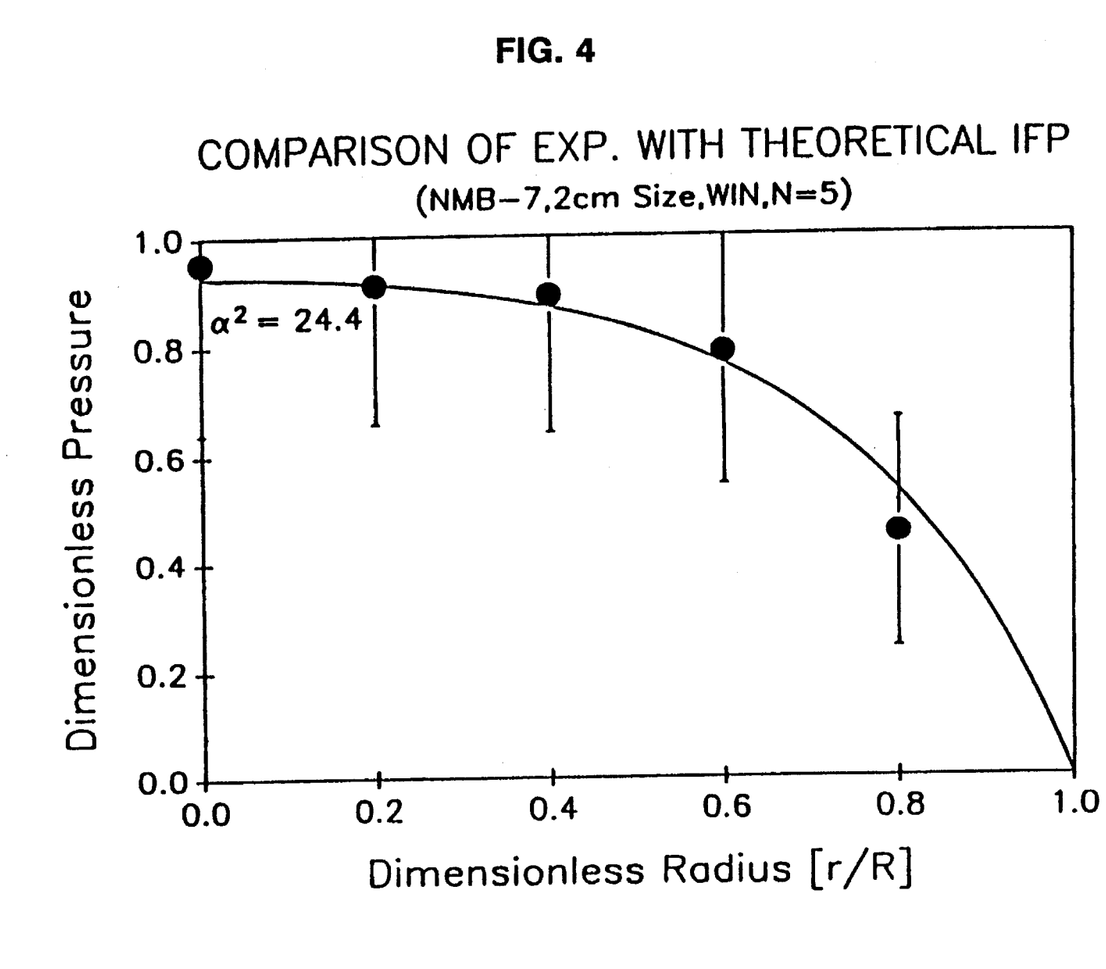
FIG. 4 is a graph illustrating interstitial fluid pressure (IFP) variation with respect to radius, before any aspiration.

II.3 Results: II.3.a Interstitial Fluid Pressure Characterization:

Interstitial Fluid Pressure (IFP) was measured as a function of tumor size at the center of the tumor. It was observed that IFP increased with the size of the tumor. IFP with respect to size appeared to plateau to 12.3±2.6 mmHg for a 3 cm diameter tumor. The theoretical and experimental IFP were compared to see the model and parameter sensitivity. To generalize the results, the radial variable was normalized to be a dimensionless radius, and the interstitial pressure was also normalized with respect to the effective vascular pressure (see FIG. 4). As a result of these normalizations the pressure profiles can be described in terms of a single parameter $\alpha$, which includes the ratio of vascular to interstitial hydraulic conductivities. Similar to the experimental data, the calculated pressure is highest in the center of a tumor and decreases down to the normal value at the tumor's edge. In addition, as parameter $\alpha$ increases, IFP rapidly reaches the effective interstitial pressure which is required to stop transcapillary filtration.

The calculated values with $\alpha^2=24.4$ were the most highly correlated with the experimental data in our neuroblastoma xenograft.

Figure 5:
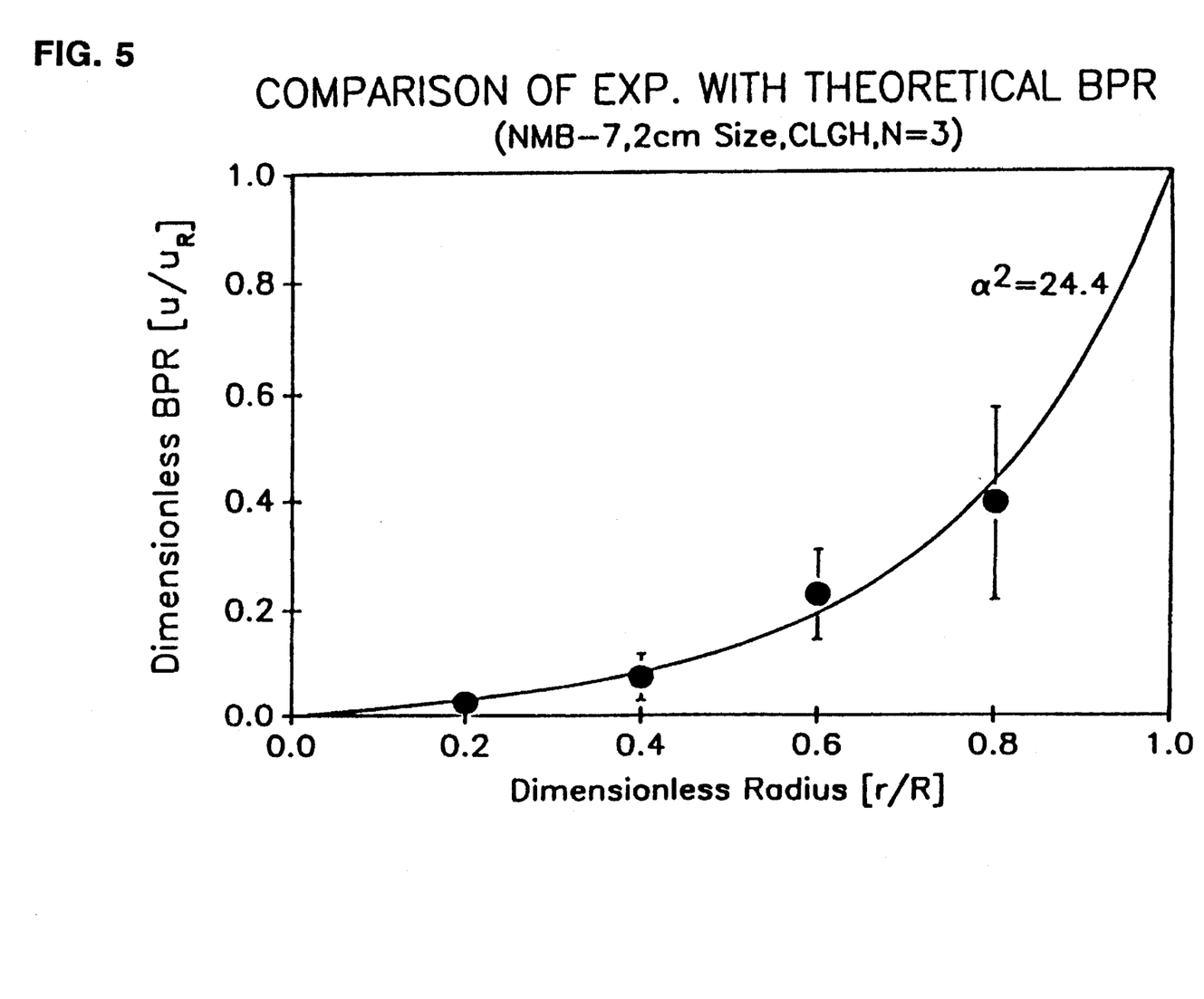
FIG. 5 is a graph illustrating the relationship between blood perfusion rate (BPR) and radius.

II.3.b Blood Perfusion Rate:

Blood Perfusion Rate (BPR) was 35.8±5.3 ml/min/100 g at the radius [r/R], 0.8 after subtracting zero flow, 12.5±3.8 ml/min/100 g. BPR profiles in neuroblastoma xenograft are shown in FIG. 5. To generalize the results, the BPR and radial axis was normalized with respect to the dimensionless radius and dimensionless BPR. The experimental data profile was fit with theoretical values based on the analytical solution when $\alpha^2=24.4$.

Figure 6:
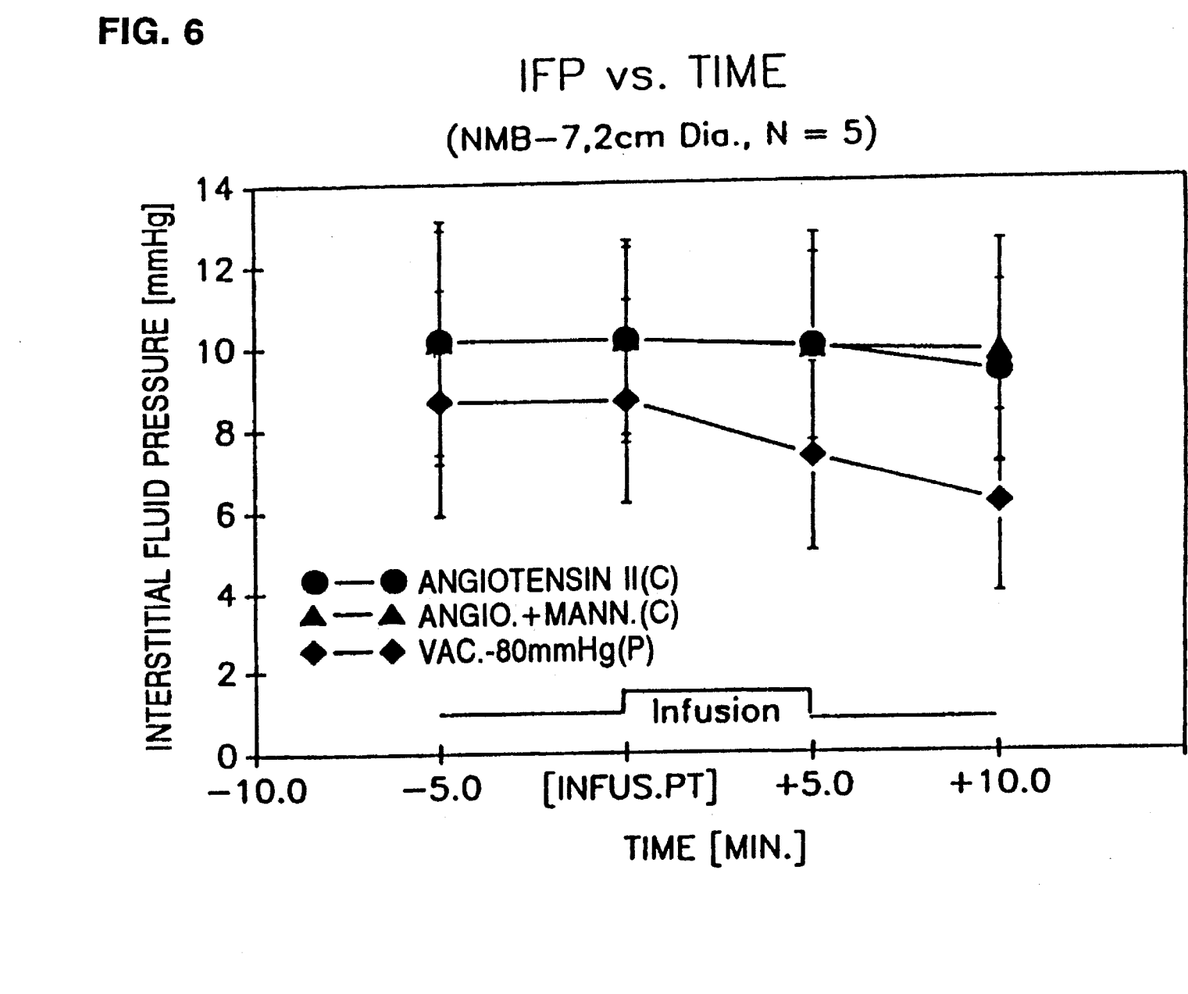
FIG. 6 is a graph illustrating manipulation impacts on interstitial fluid pressure (IFP) with respect to time.
Figure 7:
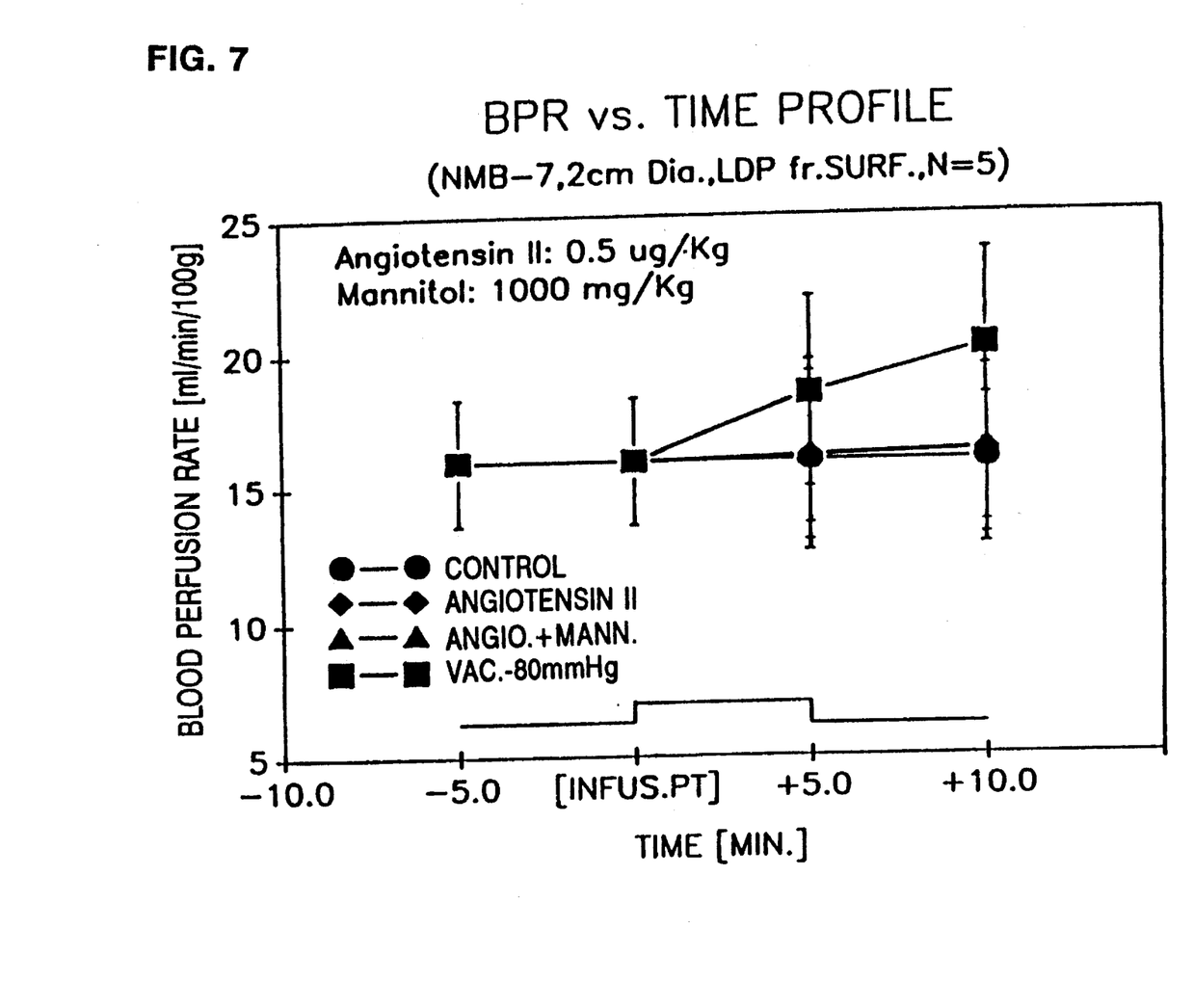
FIG. 7 is a graph illustrating manipulation impacts on blood perfusion rate (BPR) with respect to time.

II.3.c Manipulation Impact on Interstitial Fluid Pressure and Blood Perfusion Rate: Interstitial Fluid Pressure Impact in Chemical Agents:

FIGS. 6 and 7 show IFP and BPR variation by the manipulation of drug and aspiration method, and shows how these variables change at one spatial point over time (temporal distribution.) Although IFP was decreased and BPR was increased in all three cases, drug groups were not significantly different from the control group when the slopes of decreased tendency were compared by Student's t-test. On the other hand, aspiration group was significantly different from both drug and control group. ($p<0.05$).

Figure 8:
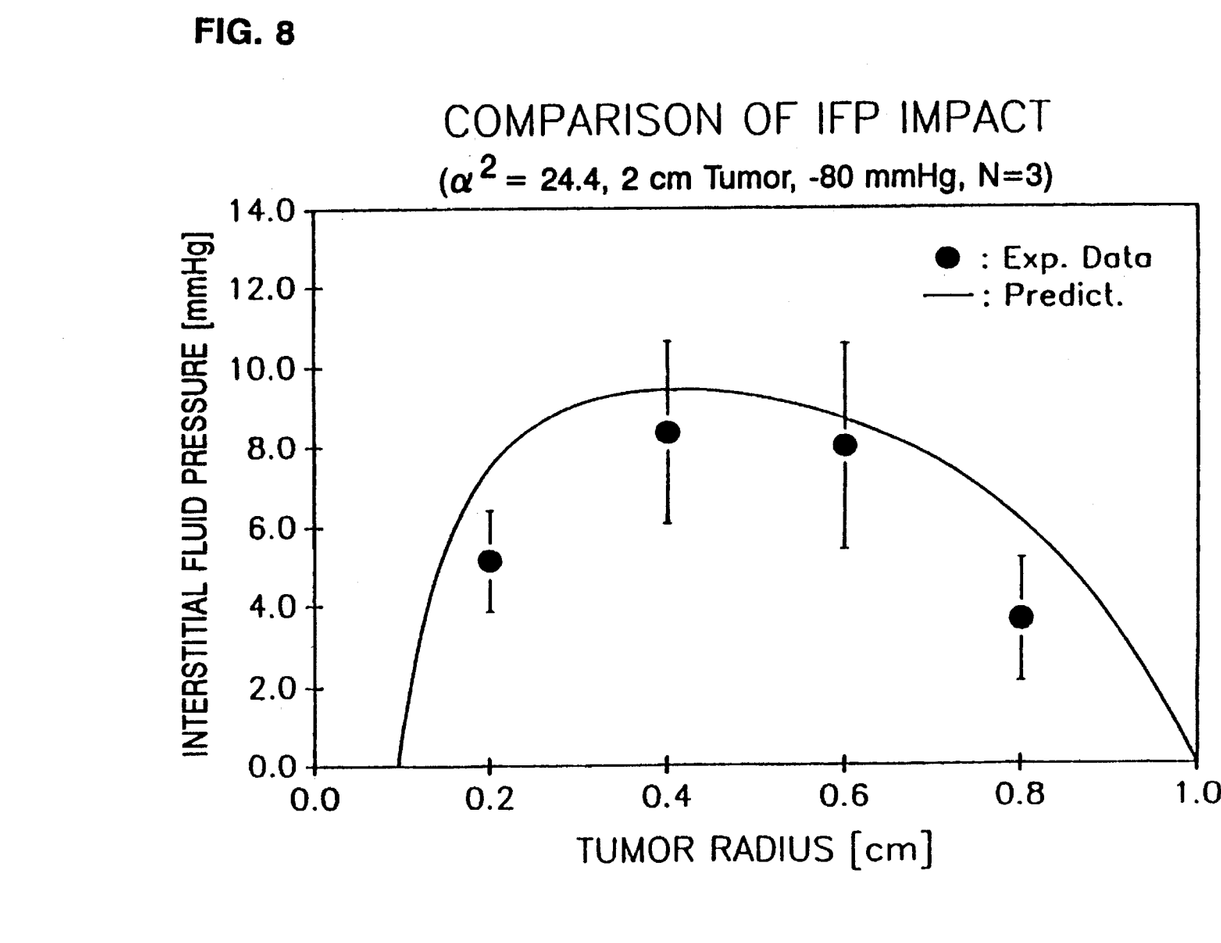
FIG. 8 is a graph illustrating the interstitial fluid pressure (IFP) distribution profile within the tumor two hours after aspiration.

FIG. 8 shows IFP distribution profile within the tumor at one point in time (2 hours after aspiration commenced) at different radius points (spatial distribution). It is clearly seen that by comparing FIGS. 4 and 8, the aspiration reduced the IFP, especially at the center of the tumor.

II.4 Conclusions:

The IFP and BPR impact of chemical agents, that is, angiotensin II and mannitol, were compared to that of aspiration. While the chemical impact was small and short-term, the aspiration impact with (−80) mmHg showed statistically significant IFP decrease and BPR increase.

III Experiment Two

Enhanced Monoclonal Antibody Transport:

Four tumor-bearing rats were divided into two groups: control (no aspiration) and aspiration group (vacuum pressure=(−80 mmHg)). 350 µCi MoAb 3F8 conjugated with $I^{131}$ was i.v. injected into the control group and into the aspiration group following two hours of aspiration. The aspiration group received an additional six hour aspiration postinjection. On the second day, we performed another six hour aspiration. At 72 hours postinjection of conjugated MoAb, the rats were sacrificed and the tumor's $I^{125}$ accumulation was measured by scintillography. Control group animals were subjected to identical experimental conditions except that no negative pressure was delivered to the tumor center. The control group animals were placed under general anesthesia and a hyperdermic needle was inserted into the tumor's center. While the sample was relatively small (N=2), the results showed a 75% increase on average in the aspiration group compared to control group. Statistical analysis was not performed because the sample population was too small.

Although a preferred embodiment has been shown and described, numerous variations and modifications will readily occur to these skilled in the art without departing from the spirit and scope of the invention. The invention is not limited to the embodiment illustrated, and its scope is limited only by way of the following claims.

References

1. Algire, G. H., Legallais, F. Y., Vascular Reactions of Normal and Malignant Tissues In Vivo, IV. The Effect of Peripheral Hypotension on Transplanted Tumors. J. Nat'l. Cancer Inst. 12: 399–421, 1951
2. Aukland, K., et al., Measurement of local blood flow with hydrogen gas. Circulation Res., 14:164, 1964.
3. Baxter, L. T., Jain, R. K., Transport of Fluid and Macromolecules in Tumors: I. Role of Interstitial Pressure and Convection. Microvas. Res. 37: 77–104, 1989.
4. Bogard, W. C., Jr., Dean, R. T., Deo, Y., Fuchs, R., Mattis, J. A., McLean, A. A., Berger, H. J. Practical Considerations in the Production, Purification, and Formulation of Monoclonal Antibodies for Immunoscintigraphy and Immunotherapy. Sem. In Nucl. Med., 19(3): 202–220, 1989.
5. Butler, T. P., Grantham, F. H., Gullino, P. M. Bulk Transfer of Fluid in the Interstitial Compartment of Mammary Tumors. Cancer Res. 35: 512–516, 1975.
6. Cheung, N. K., Saarinen, U. M., Neely, J. E., Landmeier, B., Donovan, D., Coccia, P. F. Monoclonal Antibodies to a Glycolipid Antigen on Human Neuroblastoma Cells. Cancer Res., 45: 2642–2649, 1985.
7. Cliff, W. J. Kinetics of Wound Healing in Rabbit Ear Chambers: A Time Lapse Cinemicroscopic Study. Q.J. Exp. Physiol. Log. Med. Sic., 50: 79–89, 1965.
8. DiResta, G. R., Kiel, J. W., Riedel, G. L., Kaplan, P., Shepherd, A. P. Hybrid Blood Flow Probe for Simultaneous $H_2$ Clearance and Laser-Doppler Velocimetry. Am. J. Physiol., 16: G573–G581, 1987.

9. Eddy, H. A., Casarett, G. W. Development of the Vascular System in the Hamster Malignant Neurilemmoma. Microvasc. Res. 6: 63–82, 1973.

10. Gerlowski, L. E., Jain, R. K. Microvascular Permeability of Normal and Neoplastic Tissues. Microvasc. Res. 31: 288–305, 1986.

11. Hammersen, F. The Terminal Vascular Bed in Skeletal Muscle with Special Regard to the Problem of Shunts, in: *Capillary Permeability*, Crone, C., Lassen, N. A., eds. Academic Press, 351–365, 1970.

12. Hauck, G. Physiology of the microvascular system. Angiologica 8:236–260, 1971.

13. Hori, K., Suzuki, M., Abe, I., Saito, S. Increased Tumor Pressure in Association With the Growth of Rat Tumors. Japan J. Cancer Res. (Gann) 77: 65–73, 1986.

14. Ide, A. D., Baker, N. H., Warren, S. H. Vascularization of the Brown-Pearce Rabbit Epithelioma Transplant as Seen in the Transparent Ear Chamber. Am. J. Roentgenol. 42: 891–899, 1939.

15. Intaglietta, M., Richardson, D. R., Tompkins, W. R. Blood Pressure, Flow, and Elastic Properties of Microvessels of Cat Omentum. Am. J. Physiol., 221: 922–928, 1971.

16. Jain, R. K. Transport of Molecules in the Tumor Interstitium: A Review. Cancer Res., 47: 3039–3051, 1987.

17. Jain, R. K. Commentary: Delivery of Novel Therapeutic Agents in Tumors: Physiological Barriers and Strategies. J. Nat'l. Cancer Inst., 81: 570–576, 1989.

18. Jain, R. K. Determinants of Tumor Blood Flow; A Review. Cancer Res. 48: 2641–2658, 1988.

19. Jain, R. K. Physiological Barriers to Delivery of Monoclonal Antibodies and Other Macromolecules in Tumors. Cancer Res. (Suppl.), 50: 814s–819s, 1990.

20. Jain, R. K. Transport of Macromolecules in Tumor Micro-Circulation. Biotechnol. Prog., 1: 81–94, 1985.

21. Jain, R. K. Vascular and Interstitial Barriers to Delivery of Therapeutic Agents in Tumors. Cancer and Metas. Rev., 9: 253–266, 1990.

22. Jain, R. K., Baxter, L. T. Mechanisms of Heterogeneous Distribution of Monoclonal Antibodies and Other Macromolecules in Tumors: Significance of Elevated Interstitial Pressure. Cancer Res., 48: 7022–7032, 1988.

23. Jain, R. K., and Wei, J. Dynamics of Drug Transport in Solid Tumors: Distributed Parameter Model. J. Bioengineering, 1: 313–330, 1977.

24. Kohler, G., and Milstein, C., Continuous Cultures of Fused Cells Secreting Antibody of Predefined Specificity. Nature 256:495–497, 1975.

25. Koshu, K., Kamiyama, K., Oka, N., Endo, S., Takaku, A., Saito, T. Measurement of regional blood flow using hydrogen gas generated by electrolysis. Stroke 13:483–487, 1982.

26. Lockwood, A. H., Kenny, P. J. Serial Measurements of Positron-Emitting Isotope Activity in Rat Brain. Stroke, 12(2): 173–176, 1981.

27. Neuwelt, E. A, Sprecht, H. D., Barnett, P. A., Dahlborg, S. A., Miley, A., Larson, S. M., Brown, P., Eckerman, K. F., Hellström, K. E., Hellström, I. Increased Delivery of Tumor Specific Monoclonal Antibodies to Brain After Osmotic Blood-Brain Barrier Modification in Patients With Melanoma Metastatic to Central Nervous System. Neurosurgery, 20: 885–895, 1987.

28. Newman, M. E. New Cancer Statistics Show Losses, Gains. J. Nat'l. Cancer Inst. 82(15): 1238–1239, 1990.

29. Ogston, A. G., Michel, C. C. General Descriptions of Passive Transport of Neutral Solute and Solvent Through Membranes. Prog. Biophys. Mol. Biol. 34: 197–217, 1978.

30. Paskins-Hurlbart, A. J., Hollenberg, N. K., Abrams, H. L. Tumor Perfusion in Relation to the Rapid Growth Phase and Necrosis, Studies on the Walker Carcinoma in the Rat Testicle. Microv. Res. 24: 15–24, 1982.

31. Peters, W., Teixeira, M., Intaglietta, M., Gross, J. f. Microcirculatory Studies in Rat Mammary Carcinoma, I. Transport Chamber Method, Development of Microvasculature and Pressures in Tumor Vessels. J. Nat'l. Cancer Inst. 65: 631–642, 1980.

32. Phelps, M. E., Hoffman, E. J., Selin, C., Huang, S. C., Robinson, G., McDonald, N., Schelbert, H., Kuhl, D. E. Investigation of [$^{18}$F]2-fluoro-2-deoxyglucose for the Measure of Myocardial Glucose Metabolism. J. Nucl. Med., 19: 1311–1319, 1978.

33. Roberts, P. A., Pollay, M., Engles, C., Pendleton, B., Reynolds, E., Stevens, F. A. Effect on Intracranial Pressure of Furosemide Combined With Varying Doses and Administration Rates of Mannitol. J. Neurosurg., 66: 440–446, 1987.

34. Shenkin, H. A., Goluboff, B., Haft, H. The Use of Mannitol for the Reduction of Intracranial Pressure in Intracranial Pressure in Intracranial Surgery. J. Neurosurg., 19: 897–901, 1962 .

35. Shepherd, A. P., Riedel, G. L., Ward, W. F. Laser-Doppler Measurements of Blood Flow Within the Intestinal Wall and on the Surface of the Liver. in: Microcirculation of the Alimentary Tract, edited by Koo, A., et al., Singapore: Word Scientific, p. 115–129, 1983.

36. Stosseck, K., Lübbers D. W., Cottin, N. Determination of local blood flow (microflow) by electrochemically generated hydrogen. Pflügers Archiv—European Journal of Physiology, 348:225–238, 1974.

37. Warren, B. A. The Ultrastructure of the Microcirculation of the Advancing Edge of Walker 256 Carcinoma. Microvasc. Res.,2: 443–453, 1970.

38. Wiig, H., Tveit, E., Hultborn, R., Reed, R. K., Weiss, L. Interstitial Fluid Pressure in DMBA—Induced Rat Mammary Tumors. Scand. J. Clin. Lab. Invest., 42: 159–164, 1982

39. Wikstrand, C. J., and Bigner, D. D. Cancer Research 42: 267–275, 1982.

40. Wilkinson, G. R., Shand, D. G. A Physiological Approach to Hepatic Drug Clearance. Clin. Pharmacol. Ther., 18, 377–390, 1975.

41. Yamaura, H., Sato, H. Quantitative Studies on the Developing Vascular System of Rat Hepatoma. J. Nat'l. Cancer Inst. 53: 1229–1240, 1974.

42. Young, J. S., Griffith, H. D. The Dynamics of Parenchymatous Embolism in Relation to the Dissemination of Malignant Tumors. J. Pathol. Bacteriol., 62: 293–311, 1950.

What is claimed is:

1. An apparatus for reducing interstitial fluid pressure in a tumor comprising:

an aspiration device having a plurality of aspiration tubes connected to a manifold means, each of said tubes having a plurality of aspiration holes;

means for connecting the manifold means to a suction source for creating suction inside the aspiration tubes, having a pressure value less than the interstitial fluid pressure but having a pressure value which will not result in removing or damaging the tumor, to thereby reduce the interstitial fluid pressure inside the tumor when the tubes are located in the tumor; and a measurement probe mounted to one of the plurality of aspiration tubes for measuring the interstitial fluid pressure within the tumor, wherein an aperture of the measurement probe is spaced apart from the aspiration tube to which it is mounted at a sufficient distance so that a pressure measured by the measurement probe is not substantially affected by the suction present at the plurality of aspiration holes of the plurality of aspiration tubes.

2. The apparatus according to claim 1, further comprising:

control means connected to said measurement probe; and a suction source operatively connected to said control means being responsive to a signal sent therefrom, said suction source being adapted to regulate the suction created in dependence on the signal sent from the control means, said signal being indicative of the pressure measured by the measurement probe, wherein the suction has a pressure value less than the interstitial fluid pressure, to thereby reduce the interstitial fluid pressure within the tissue.

3. A process for reducing interstitial fluid pressure in a tumor comprising:

placing an aspiration device within the tumor; and applying, to the aspiration device, suction having a pressure value less than the interstitial fluid pressure but having a pressure value which will not result in removing or damaging the tumor, to thereby reduce interstitial fluid pressure within the tumor, wherein the step of placing an aspiration device comprises locating within the tumor an aspiration device of diameter not greater than that of an 18 gauge needle having a plurality of aspiration holes, and wherein the pressure value of the suction applied in the step of applying suction is greater than −100 mmHg.

4. The process according to claim 3, wherein the step of placing an aspiration device comprises locating an aspiration device having a plurality of aspiration tubes for locating in the tumor, each tube having at least one aspiration hole.

5. The process according to claim 4, wherein each tube has a plurality of aspiration holes.

6. The process of claim 3, used in conjunction with chemotherapy to enhance treatment of inoperable tumors.

7. The process of claim 3, used in conjunction with radiation therapy to enhance treatment of inoperable tumors.

8. A process for reducing interstitial fluid pressure in a tumor comprising:

placing an aspiration device within the tumor;

applying, to the aspiration device, suction having a pressure value less than the interstitial fluid pressure but having a pressure value which will not result in removing or damaging the tumor, to thereby reduce interstitial fluid pressure within the tumor;

measuring the interstitial fluid pressure within the tumor; and regulating suction applied to the aspiration device in dependence on the measured interstitial pressure wherein the suction has a pressure value less than the interstitial fluid pressure but has a pressure value which will not result in removing or damaging the tumor, to thereby reduce the interstitial fluid pressure within the tumor.

9. A process for reducing interstitial fluid pressure in a tumor comprising:

placing an aspiration device within the tumor; and applying, to the aspiration device, suction having a pressure value less than the interstitial fluid pressure but having a pressure value which will not result in removing or damaging the tumor, to thereby reduce interstitial fluid pressure within the tumor, wherein the aspiration device has means for measuring the interstitial fluid pressure, and wherein through control means connected to the means for measuring the interstitial fluid pressure and suction source, the suction created may be regulated in dependence on the measured interstitial fluid pressure so that the suction is maintained at a pressure value below the interstitial fluid pressure.

* * * * *